(12) United States Patent
Rufo et al.

(10) Patent No.: US 9,072,728 B2
(45) Date of Patent: Jul. 7, 2015

(54) TREATMENT OF SEVERE DISTAL COLITIS

(75) Inventors: Paul Rufo, West Roxbury, MA (US); Wayne I. Lencer, Jamaica Plain, MA (US)

(73) Assignee: Children's Medical Center Corporation, Boston, MA (US)

( * ) Notice: Subject to any disclaimer, the term of this patent is extended or adjusted under 35 U.S.C. 154(b) by 1207 days.

(21) Appl. No.: 10/572,667

(22) PCT Filed: Sep. 20, 2004

(86) PCT No.: PCT/US2004/030813
§ 371 (c)(1),
(2), (4) Date: Jan. 13, 2009

(87) PCT Pub. No.: WO2005/027851
PCT Pub. Date: Mar. 31, 2005

(65) Prior Publication Data
US 2009/0118343 A1 May 7, 2009

Related U.S. Application Data

(60) Provisional application No. 60/504,516, filed on Sep. 18, 2003.

(51) Int. Cl.
*A61K 31/4174* (2006.01)

(52) U.S. Cl.
CPC ................................. *A61K 31/4174* (2013.01)

(58) Field of Classification Search
CPC ................................................. A61K 31/4174
See application file for complete search history.

(56) References Cited

U.S. PATENT DOCUMENTS

| | | | |
|---|---|---|---|
| 4,478,822 A | 10/1984 | Haslam et al. | |
| 4,698,359 A | 10/1987 | Niederer et al. | |
| 5,273,992 A | 12/1993 | Brugnara et al. | |
| 5,348,746 A | 9/1994 | Dong et al. | |
| 5,358,959 A | 10/1994 | Halperin et al. | |
| 5,512,591 A | 4/1996 | Halperin et al. | |
| 5,585,115 A | 12/1996 | Sherwood et al. | |
| 5,599,795 A | 2/1997 | McCann et al. | |
| 5,633,274 A | 5/1997 | Halperin et al. | |
| 6,121,299 A | 9/2000 | Kozak et al. | |
| 6,207,703 B1 | 3/2001 | Ponikau | |
| 6,258,374 B1 | 7/2001 | Friess et al. | |
| 6,291,500 B2 | 9/2001 | Ponikau | |
| 6,331,534 B1 | 12/2001 | Berliner et al. | |
| 6,348,316 B1 | 2/2002 | Taylor et al. | |
| 6,383,471 B1 | 5/2002 | Chen et al. | |
| 6,482,826 B1 | 11/2002 | Pierard | |
| 6,495,567 B1 | 12/2002 | Lencer et al. | |
| 6,545,028 B2 | 4/2003 | Jensen et al. | |
| 6,946,118 B1 | 9/2005 | Lawter et al. | |
| 2002/0035096 A1 | 3/2002 | Lawter et al. | |
| 2002/0045604 A1 | 4/2002 | Lawter et al. | |
| 2002/0052390 A1* | 5/2002 | Ponikau | 514/310 |

FOREIGN PATENT DOCUMENTS

| | | |
|---|---|---|
| WO | WO 00/30626 A2 | 6/2000 |
| WO | WO 02/078648 | 10/2002 |

OTHER PUBLICATIONS

Mimura T, Rizzello F, Helwig U, Poggioli G, Schreiber S, Talbot IC, Nicholls RJ, Gionchetti P, Campieri M, and Kamm MA, "Four-week open-label trial of metronidazole and ciprofloxacin for the treatment of recurrent or refractory pouchitis," Alimentary Pharmacology & Therapeutics, May 2002, 16(5), 909-917.*
Tracy JW and Webster LT, Chapter 41 Drugs use in the Chemotherapy of Protozoal Infections (continued)Infections, "Goodman & Gilman's The Pharmacological Basis of Therapeutics, 10th ed." Hardman JG, Limbird LE, and Gilman AG, Eds., McGraw-Hill, 2001, 1097-1120 (pp. 1097 and 1105-1108 provided).*
Clinicaltrials.gov. Clotrimazole Enemas for Pouchitis in Children and Adults. Aug. 20, 2003.*
Olumide F, Adesola AO. Metronidazole retention enema in the management of severe intestinal amoebiasis. Niger Med J. Jan. 1976;6(1):2-8 (abstract only provided).*
Parsad D, Pandhi R, Negi KS, Kumar B. Topical metronidazole in seborrheic dermatitis—a double-blind study. Dermatology. 2001;202(1):35-7.*
U.S. Appl. No. 08/307,874, filed Sep. 16, 1994.
U.S. Appl. No. 08/307,887, filed Sep. 16, 1994, Halperin.
Collins, Cimetidine-induced acute ulcerative colitis. Med J Aust. Apr. 3, 1982;1(7):307.
Gamborg, In vitro antifungal effect of metronidazole on pityrosporum ovale. Mykosen, Deutsprachige Mykologische Gesellschaft. Jun. 1, 1984;27(1):475-6.
Gionchetti et al., Diagnosis and treatment of pouchitis. Best Pract Res Clin Gastroenterol. Feb. 2003;17(1):75-87.
Nielsen, In vitro antifungal effect of metronidazole on pityrosporum ovale. Mykosen, Deutspachige Mykologische Gesellschaft. Jun. 1, 1984;27(9):475-6.
Nix et al., Pharmacodynamics of metronidazole determined by a time-kill assay for Trichomonas vaginalis. Antimicrob Agents Chemother. Aug. 1995;39(8):1848-52.
Singh et al., Cimetidine therapy and duodenal candidiasis: role in healing process. Indian J Gastroenterol. Jan. 1992;11(1):21-2.
Chambers, Chapter 50: Miscellaneous antimicrobial agents; disinfectants, antiseptics, & sterilants. In *Basic & Clinical Pharmacology*, Eighth Edition, Ed. Katzung. McGraw-Hill. 2001;845-53.
Phillips et al., Chapter 40: Chemotherapy of protozoal infections: amebiasis, giardiasis, trichomoniasis, trypanosomiasis, leishmaniasis, and other protozoal infections. In *The Pharmacological Basis of Therapeutics*, Eleventh Edition, Eds. Shanahan et al. Lange Medical Books/McGraw-Hill. 2006;1049-72.
Brugnara et al., Therapy with oral clotrimazole induces inhibition of the Gardos channel and reduction of erythrocyte dehydration in patients with sickle cell disease. J Clin Invest. Mar. 1, 1996;97(5):1227-34.

* cited by examiner

*Primary Examiner* — Paul Zarek
(74) *Attorney, Agent, or Firm* — Wolf, Greenfield & Sacks, P.C.

(57) ABSTRACT

This invention relates to methods and materials involved in the treatment of diseases with severe distal colitis component, and more specifically non-fungal and/or non-microbial induced mucositis of the distal intestinal tract. Kits and pharmaceutical compositions for medical treatments also are provided.

9 Claims, 8 Drawing Sheets

TREATMENT OF SEVERE DISTAL COLITIS

RELATED APPLICATIONS

This application is a national stage of PCT/US2004/030813 filed Sep. 20, 2004, which claims the benefit under 35 U.S.C. 119(e) of U.S. provisional Patent Application No. 60/504,516 filed Sep. 18, 2003, the disclosures of both of which are incorporated herein by reference.

FEDERALLY SPONSORED RESEARCH

This invention was made with Government support under Grant No. FD-R-002017 awarded by the National Institutes of Health. The Government has certain rights to this invention.

BACKGROUND OF INVENTION

This invention relates to methods and materials involved in the treatment of non-fungal induced mucositis of the distal intestinal tract, including pouchitis.

Total abdominal colectomy with the subsequent creation of an ileal pouch (IPAA) has become the treatment of choice for unremitting ulcerative colitis and polyposis syndromes. The development of an idiopathic acute and active chronic inflammation in these surgically constructed ileal reservoirs, a clinical entity referred to as pouchitis, is the most common long-term complication of this procedure. The incidence of pouchitis is cumulative and ultimately effects 50-60% of pediatric and adult patients with ulcerative colitis in this country (or about 75,000 patients in total) who undergo colectomy. Its prevalence appears to be similar in pediatric and adult patient populations.

The pathogenesis of pouchitis remains a mystery. As such, treatments for this disorder have been largely empiric and have relied on the use of oral or topically applied antibiotics or immunosuppressive agents. However, there is a growing body of patients with pouch disease that is refractory to all presently available therapies. Persistent pouch inflammation in these patients, manifest clinically as abdominal cramping, rectal bleeding, and fecal incontinence can be medically and socially disabling.

The transmigration of polymorphonuclear white blood cells (PMNs) across intestinal epithelia contributes to the mucosal damage that occurs in infectious and inflammatory gastrointestinal diseases including pouchitis. Effective pharmacologic approaches to reduce or eliminate this cellular response could have a high impact on the clinical outcome of patients experiencing intestinal inflammation.

Certain azole compounds such as clotrimazole have been used both topically and systemically as antifungals. For example, U.S. Pat. No. 6,207,703 teaches the use of these antifungal compounds for the treatment of diseases associated with fungal infections; non-invasive fungus induced conditions such as chronic otitis media, chronic colitis and Crohn's disease. More recently, studies have identified other uses for such imidazoles. U.S. Pat. No. 5,273,992 revealed that these imidazoles regulate $Ca^{++}$ activated $K^+$ channels in erythrocytes, and are thus useful in treating sickle cell anemia, which involves the inhibition of potassium transport; and U.S. Pat. No. 6,495,567 teaches the use of azoles for the treatment of diarrhea and scours. Similarly, U.S. Pat. No. 6,545,028 discloses that certain azole compounds, including clotrimazole (CLT), because of their inhibitory activity on $Ca^{++}$ activated potassium channels can be used for the treatment of diseases such as inflammatory bowel disease, Crohn's disease, dermatitis, psoriasis etc. These azoles have also been found to be effective in inhibiting endothelial and/or vascular smooth muscle cell proliferation. The results of this finding are described in U.S. Pat. No. 5,358,959 and U.S. Ser. No. 08/018,840, which discloses using clotrimazole for treating atherosclerotic and angiogenic conditions, respectively. Non-imidazole metabolites and analogs of the foregoing compounds also have been described as useful in treating the foregoing conditions (see U.S. Ser. Nos. 08/307,874 and 08/307,887). Clotrimazole also has been found to inhibit cellular proliferation and has been proposed as an anti-cancer agent. It was subsequently discovered that the anti-proliferative effects were mediated by the tri-aryl portion of the molecule, and tri-aryl derivatives were proposed for inhibiting cancer cell growth and cellular proliferation responsible for inflammatory diseases. (See U.S. Pat. No. 6,331,534).

Previous studies have demonstrated that CLT and related antifungal agents inhibit the chemotaxis of PMNs across membrane filters. Previous investigators have demonstrated that CLT and related antifungal compounds have been shown to affect PMN migration towards chemotactic gradients in-vitro without effecting PMN function or antimicrobial activity as assessed by in-vitro killing assays. These in-vitro effects prompted an evaluation of the potential clinical utility of oral CLT therapy in the treatment of rheumatoid arthritis, a disorder characterized histologically by the recruitment of activated PMN's across synovial membranes and into joint spaces. Outcome data from these studies did not reach statistical significance, and the adverse effects associated with systemic administration of CLT proved to be dose-limiting.

SUMMARY OF INVENTION

It has been now discovered, surprisingly, that CLT (and related azole antifungal agents) can be used for treating mucositis of the distal intestinal tract if administered locally in an effective amount. The mucositis can be non-fungal induced mucositis, and/or non-microbial induced mucositis. It is believed that the distal components of non-fungal and/or non microbial induced mucositis are not treatable by conventional dosing because of low local concentrations of therapeutics. High conventional oral dosing results in undesired side-effects. This invention allows for treatment of the non-fungal and/or non-microbial induced mucositis of the distal intestinal tract because the disease can be reached for example by enema, suppository or an enteric coated tablet, and an effective amount of the therapeutic can be delivered directly to the distal intestinal tract. If the enema therapy delivery reaches non-distal regions this therapy could also extent to other non-distal regions.

It has been discovered, surprisingly, that CLT (and related azole antifungal agents) inhibits IL-8 secretion and inhibit the inflammatory process. By inhibiting the activities of cell types that both orchestrate (intestinal epithelial cells) as well as mediate (activated PMN's) intestinal inflammation, topical CLT therapy represents a novel treatment strategy in the management of patients with pouchitis and other inflammatory or infectious colitis. CLT can be used to treat the inflammation of mucosal tissue that is a serious problem affecting millions of people world-wide.

According to one aspect of the invention, a method is provided for treating a subject having non-fungal and/or non-microbial induced mucositis of the distal intestinal tract. The method involves administering locally to the distal intestinal tract of the subject an anti-fungal azole compound in an amount effective to reduce or eliminate the non-fungal and/or non-microbial induced mucositis of the distal intestinal tract.

The effective amount is local delivery of a single dosage of about 2,000 mg to 10,000 mg of anti-fungal azole compound, at a frequency of the administration from four times a day to once a month. In important embodiments the administration is via enema therapy, suppository or by enteric coated tablets. In important embodiments, the non-fungal and/or non-microbial induced intestinal mucositis is selected from the group consisting of: pouchitis, ulcerative colitis, Crohn's disease, allergic colitis, autoimmune colitis, autoimmune enteropathy, bacterial colitis, diversion colitis and lymphocytic colitis.

In certain embodiments of the invention the intestinal mucositis is an IL-8 mediated disorder discussed herein. In yet other embodiments of the invention the intestinal mucositis is an IL-8 mediated disorder not specifically discussed herein, but readily treatable by the methods of the present invention practiced by one of ordinary skill in the art. In a particularly important embodiment, the intestinal mucositis is pouchitis and the subject is a human.

The term pouchitis refers to a clinical entity characterized by the development of an idiopathic acute and active chronic inflammation in surgically constructed ileal reservoirs following total abdominal colectomy, and it is the most common long-term complication of this procedure. The present invention shows that, surprisingly, enema therapy with anti-fungal azole compounds can be an effective treatment for pouchitis. In important embodiments, the anti-fungal azole compound is selected from the group consisting of: anti-fungal imidazole compounds, anti-fungal triazole compounds and anti-fungal nitroimidazole compounds. Preferably, the anti-fungal azole compound is an anti-fungal imidazole compound, and most preferably the anti-fungal imidazole compound is clotrimazole.

In important embodiments, the anti-fungal azole compound is administered as an enema. In one such embodiment, the effective amount is a dose of about 2,000 mg to about 10,000 mg of the anti-fungal azole compound at a frequency of administration from four doses a day to once every month. In another such embodiment, the effective dose of about 2,500 mg to about 10,000 mg of the anti-fungal azole compound at a frequency of administration from two doses a day to one every two weeks. In one important embodiment the dose is about 2,500 to about 4000 mg per day.

The method further includes co-administration of a drug other than the anti-fungal azole compound. The drug can be an agent useful for treating a non-fungal and/or non-microbial induced inflammatory condition. Such drugs include, for example, those useful in treating any of the conditions recited above. Important such drugs are anti-inflammatory agents and anti-bacterial agents. Anti-inflammatory agents can be steroidal or nonsteroidal anti-inflammatory agents. A list of such agents is described below, each member of which as if expressly recited herein. Important agents are those which are useful for treating intestinal mucositis, including each of the conditions described above.

According to another aspect of the invention, an article of manufacture is provided. The article of manufacture includes packaging material and an anti-fungal azole compound, and additionally a label or package insert indicating that the anti-fungal azole compound can be administered to a subject for treating mucositis of the distal intestinal tract. The label or insert optimally indicates a dose range of 2,000 to 10,000 mg administered from four times a day to once a month, and preferably from two times a day to once every two weeks, and more preferably once per day. The anti-fungal azole compound can be provided in single unit dosages each containing an amount of about 2,000 mg to about 10,000 mg of anti-fungal azole compound, and more preferably 2,500 mg to 10,000 mg of anti-fungal azole compound. Alternatively, multiple unit dosages can be provided total the effective dose. In one important embodiment, the label or package insert indicates that the anti-fungal compound can be administered to treat non-fungal and/or non-microbial induced mucositis. In one important embodiment, the label or package insert indicates that the anti-fungal compound can be administered to a human subject. In a preferred embodiment, the anti-fungal azole compound is clotrimazole. The compound can be in a powdered form and the article of manufacture can include a diluents in a container for dissolving the compound. The compound also can be in a liquid form already dissolved, concentrated or in a formulation that is ready to use. In one embodiment the formulation is for rectal administration.

The article of manufacture also can further include an enema component. In one embodiment, the enema component is either or both of an insertable enema tip or a container adapted for fluid connection with an insertable enema tip. In one such embodiment the container is a soft squeeze bottle. The article of manufacture can further include one or more of: a flow-control valve, a reflux-prevention valve, and a replaceable protective shield for the insertable enema tip. The article of manufacture in one important embodiment is disposable. The article of manufacture in another important embodiment is latex free.

According to another aspect of the invention a pharmaceutical composition is provided, wherein enteric coated tablets contain anti-fungal azole compounds. The enteric coated tablets release the anti-fungal azole compound in the distal intestinal tract. The enteric coated tablets release the anti-fungal azole compound in intestinal fluids where the pH is greater than 5.5. In another embodiment the enteric tablets release the anti-fungal azole compound in intestinal fluids of pH greater than 7. The anti-fungal azole compound is present in an amount of about 2,000 mg to about 10,000 mg doses, and more preferably 2,500 mg to 10,000 mg doses. In a preferred embodiment, the anti-fungal azole compound is clotrimazole. The enteric coated tablets are administered to treat non-fungal and/or non-microbial induced mucositis.

These and other aspects of the invention are described in further detail below.

DETAILED DESCRIPTION

Figure 1:
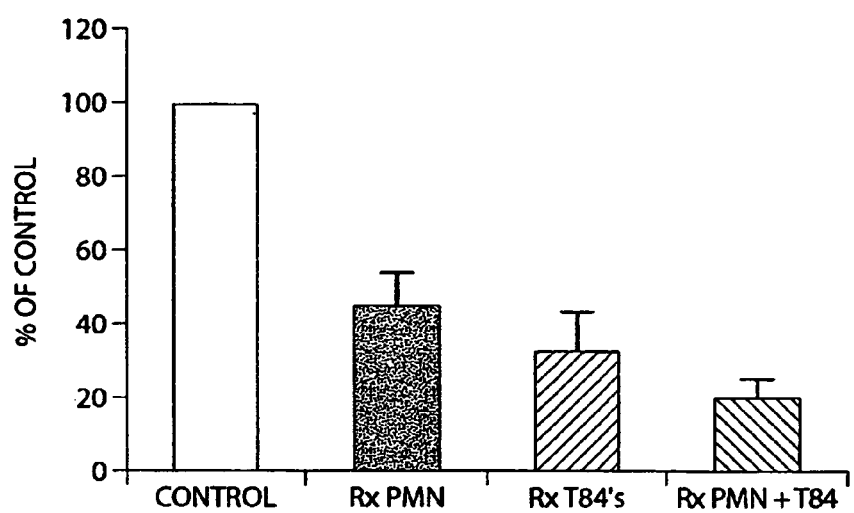
FIG. 1 is a bar graph that shows the effect of clotrimazole on human PMN transmigration across intestinal T84 cell monolayers.

The phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

The methods and products of the invention are applied in medical settings for the treatment of non-fungal induced mucositis of the distal intestinal tract. Local dosage at high levels are an important element of the invention. According to this aspect of the invention, the dosage is delivered locally in the distal intestinal tract, for example by enema or by enteric coated tablets which deliver and release locally in the distal intestinal tract. Such 'topical' doses are described in greater detail in the summary of the invention and in the examples, and typically are in the range of 2,000 mg to 10,000. Preferably the dosage is from 2,500 mg to 10,000 mg. The frequency of such dosage is preferably in the range of from four times per day to once per month. In an important embodiment, the dosage is from 2,500 mg to 10,000 mg by enema, once per day.

Non-fungal induced inflammation is essentially any inflammation except for one caused by a fungus. Non-microbial induced inflammation is essentially any inflammation except for one caused by a microbe. The term "mucositis" refers to inflammation affecting one or more layers of the intestinal wall (mucosa, submucosa, muscularis or serosa). A particularly important type of such inflammation is non-fungal induced mucositis of the distal intestinal tract. The term "non-fungal induced mucositis of the distal intestinal tract" means non-fungal induced mucositis, possibly having other digestive tract components, but necessarily having a severe distal colitic or ileitic component such as colitis or ileitis. The distal intestinal tract is the proximal portion of the gastrointestinal tract and includes the terminal ileum, cecum, colon, rectum and anal canal. The distal intestinal mucositis can be, but is not limited to, the group consisting of: pouchitis, inflammatory bowel disease, ulcerative colitis, Crohn's disease, allergic colitis, autoimmune colitis, autoimmune enteropathy, bacterial colitis, diversion colitis and lymphocytic colitis. In important embodiments, the pouchitis is also non-microbial induced.

In important embodiments the mucositis is non-fungal induced and/or non-microbial induced. In certain embodiments of the invention the intestinal mucositis is an IL-8 mediated disorder discussed herein. In yet other embodiments of the invention the intestinal mucositis is an IL-8 mediated disorder not specifically discussed herein, but readily treatable by the methods of the present invention practiced by one of ordinary skill in the art. In a particularly important embodiment, the intestinal mucositis is pouchitis and the subject is a human.

It is believed that the distal components of non-fungal induced mucositis are not treatable by conventional dosing because of the low local concentrations of therapeutics that are achieved. High conventional dosing results in undesired side-effects. This invention allows for treatment of the non-fungal induced mucositis of the distal intestinal tract because the disease can be reached by enema and an effective amount of the therapeutic can be delivered directly to the distal intestinal tract. If the enema therapy delivery reaches non-distal regions this therapy could also extent to other non-distal regions.

Another aspect of the invention can be applied in research settings to better understand the inflammatory process and the influence of IL-8 on the inflammatory and other processes. In general, the inflammatory response is an essential mechanism of defense of the organism against the attack of infectious agents, and it is also implicated in the pathogenesis of many acute and chronic diseases, including autoimmune disorders. In spite of being needed to fight pathogens, the effects of an inflammatory burst can be devastating. It is therefore often necessary to restrict the symptomotology of inflammation with the use of anti-inflammatory drugs. Inflammation is a complex process normally triggered by tissue injury that includes activation of a large array of enzymes, the increase in vascular permeability and extravasation of blood fluids, cell migration and release of chemical mediators, all aimed to both destroy and repair the injured tissue. Inflammation can be caused by microorganisms such as bacteria, viruses and parasites.

The active compounds to be administered are chosen from among anti-fungal azole compounds, including imidazole, nitroimidazole and triazole derivatives. All of these chemical compositions are well recognized, pharmacologically characterized, and licensed for use by the FDA today. As such, established and empirically documented parameters regarding their limited toxicity and their useful dosages as antimycotic and antiprotozoal agents are well described in the scientific and medical literature. In addition, there are few side-effects for any and no debilitating contraindications known for some of these chemical compounds. Accordingly, the chosen active compound may be administered immediately to effectively reduce the clinical manifestations and symptoms of inflammation.

One embodiment involves the administration of at least one active compound selected from the group consisting of imidazole derivatives, nitroimidazole derivatives, and triazole derivatives. Collectively, these compounds form a single chemical class of analogous structural formulations. Within the class as a whole, however, each derivative grouping has its own particular membership which share common structures and exhibit common properties. The chemical class as a whole, each group within the class, and the membership of each grouping is given by Table 1 below.

TABLE 1

Groups and examples of pharmacologically active compounds

1. IMIDAZOLE COMPOUNDS

Clotrimazole
Miconazole
Ketoconazole
Econazole
Butoconazole
Oxiconazole
Sulconazole
Tioconazole

2. TRIAZOLE COMPOUNDS

Fluconazole
Terconazole
Itraconazole

3. NITROIMIDAZOLE COMPOUNDS

Metronidazole
Tinidazole
Nimorazole

TABLE 1-continued

Groups and examples of pharmacologically active compounds

Omidazole
Benznidazole

Subjects to be treated include humans, non-human primates, dogs, cats, sheep, goats, horses, cows and rodents.

The agents of the invention are administered in effective amounts. An effective amount means that amount necessary to lessen or eliminate clinical symptoms of, delay the onset of, inhibit the progression of, or halt altogether the onset or progression of the particular condition being treated. In general, an effective amount for treating an inflammatory condition will be that amount necessary to inhibit the onset or progression of inflammation. This can be determined by observing symptoms of inflammatory conditions or by direct measurement of the extent of inflammatory cell accumulation. When administered to a subject, effective amounts will depend, of course, on the particular condition being treated; the severity of the condition; individual patient parameters including age, physical condition, size and weight; concurrent treatment; frequency of treatment; and the mode of administration. These factors are well known to those of ordinary skill in the art and can be addressed with no more than routine experimentation.

The active agents thus can be provided in pharmaceutical preparations. When administered, the pharmaceutical preparations of the invention are applied in pharmaceutically acceptable amounts and in pharmaceutically acceptable compositions. Such preparations may routinely contain salts, buffering agents, preservatives, compatible carriers, and optionally other therapeutic ingredients. When used in medicine the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrocholoric, hydrobromic, sulphuric, nitric, phosphoric, maleic, acetic, salicyclic, p-toluene sulfonic, tartaric, citric, methane sulfonic, formic, malonic, succinic, naphthalene-2-sulfonic, and benzene sulfonic. Also, pharmaceutically acceptable salts can be prepared as alkaline metal or alkaline earth salts, such as sodium, potassium or calcium salts.

Suitable buffering agents include: acetic acid and a salt (1-2% W/V); citric acid and a salt (1-3% W/V); boric acid and a salt (0.5-2.5% W/V); and phosphoric acid and a salt (0.8-2% W/V).

Suitable preservatives include benzalkonium chloride (0.003-0.03% W/V); chlorobutanol (0.3-0.9% W/V); parabens (0.01-0.25% W/V) and thimerosal (0.004-0.02% W/V).

The pharmaceutical preparations of the present invention contain an effective amount of an agent included with a pharmaceutically-acceptable carrier. The term "pharmaceutically-acceptable carrier" as used herein means one or more compatible solid or liquid filler, dilutants or encapsulating substances which are suitable for administration to a human or other animal. The term "carrier" denotes an organic or inorganic ingredient, natural or synthetic, with which the active ingredient is combined to facilitate the application. The components of the pharmaceutical compositions are capable of being commingled with the molecules of the present invention, and with each other, in a manner such that there is no interaction which would substantially impair the desired pharmaceutical efficacy. Carrier formulations suitable for oral, topical, subcutaneous, intravenous, intramuscular, etc. can be found in Remington's Pharmaceutical Sciences, Mack Publishing Company, Easton, Pa., USA.

A variety of administration routes are available. The particular mode selected will depend of course, upon the particular drug selected, the severity of the disease state being treated and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, rectal, sublingual, topical, nasal, transdermal, intradermal or parenteral routes. The term "parenteral" includes subcutaneous, intravenous, intramuscular, or infusion. Administration to mucosal surfaces is one important mode of administration, such as by oral administration, pulmonary administration, intestinal or colonic administration such as by enteric coating or enema, vaginal administration, suppository and the like. Suppository and enema administration are particularly important modes of administration when treating intestinal mucositis such as pouchitis.

The compositions may conveniently be presented in unit dosage form and may be prepared by any of the methods well known in the art of pharmacy. All methods include the step of bringing the conjugates of the invention into association with a carrier which constitutes one or more accessory ingredients. In general, the compositions are prepared by uniformly and intimately bringing the compounds into association with a liquid carrier, a finely divided solid carrier, or both, and then, if necessary, shaping the product.

Compositions suitable for oral administration may be presented as discrete units such as capsules, cachets, tablets, troches, suppositories or lozenges, each containing a predetermined amount of the active compound. Other compositions include suspensions in aqueous liquors or non-aqueous liquid such as a syrup, an elixir, or an emulsion.

Other delivery systems can include time-release, delayed release or sustained release delivery systems. Such systems can avoid repeated administrations of the active compounds of the invention, increasing convenience to the subject and the physician. Many types of release delivery systems are available and known to those of ordinary skill in the art and some are discussed in greater detail herein. They include polymer based systems such as polylactic and polyglycolic acid, polyanhydrides and polycaprolactone; nonpolymer systems that are lipids including sterols such as cholesterol, cholesterol esters and fatty acids or neutral fats such as mono-, di and triglycerides; hydrogel release systems; silastic systems; peptide based systems; wax coatings, compressed tablets using conventional binders and excipients, partially fused implants and the like. In addition, a pump-based hardware delivery system can be used, some of which are adapted for implantation.

The pharmaceutical preparations of the invention can also can be configured as a suppository. Formulations of suppositories are well known and commercially available. The anti-fungal azoles and clotrimazole can be added to such well known formulations. The anti-fungal azoles can be mixed together in solution or semi-solid solution in such formulations, can be provided in a suspension within such formulations or could be contained in particles within such formulations. The anti-fungal azole also may be in the form of vesicles, such as wax coated micropellets dispersed throughout the material of the suppository. The coated pellets can be fashioned to immediately release the opioid antagonist based on temperature, pH or the like. The pellets also can be configured so as to delay the release of the anti-fungal azole. The anti-fungal azole pellets also can be configured to release the anti-fungal azole in virtually any sustained release pattern, including patterns exhibiting first order release kinetics or sigmoidal order release kinetics using materials of the prior art and well known to those of ordinary skill in the art. The anti-fungal azole can also be contained within a core within the suppository. The core may have any one or any combination of the properties described above in connection with the pellets. The anti-fungal azoles may be, for example, in a core coated with a material, dispersed throughout a material, coated onto a material or adsorbed into or throughout a material. It should be understood that the pellets or core may be of virtually any type. They may be drug coated with a release material, drug interspersed throughout material, drug adsorbed into a material, and so on. The material may be erodible or nonerodible.

The therapeutic agent(s) of the invention, including specifically but not limited to the anti-fungal imidazoles and clotrimazole, may be provided in particles. Particles as used herein means nano or microparticles (or in some instances larger) which can consist in whole or in part of the anti-fungal imidazoles or clotrimazole or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero order release, first order release, second order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules which contain the antagonist in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described by H. S. Sawhney, C. P. Pathak and J. A. Hubell in *Macromolecules*, (1993) 26:581-587, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) including, but not limited to antifungal imidazoles or clotrimazole, may be contained in controlled release systems. The term "controlled release" is intended to refer to any drug-containing formulation in which the manner and profile of drug release from the formulation are controlled. This refers to immediate as well as nonimmediate release formulations, with nonimmediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug therefrom. "Delayed release" may or may not involve gradual release of drug over an extended period of time, and thus may or may not be "sustained release."

Delivery systems specific for the gastrointestinal tract are roughly divided into three types: the first is a delayed release system designed to release a drug in response to with, for example, a change in pH; the second is a timed-release system designed to release a drug after a predetermined time; and the third is a microflora enzyme system making use of the abundant enterobacteria in the lower part of the gastrointestinal tract (e.g., in a colonic site-directed release formulation).

An example of a delayed release system is one that uses, for example, an acrylic or cellulosic coating material and dissolves on pH change. Because of ease of preparation, many reports on such "enteric coatings" have been made. In general, an enteric coating is one which passes through the stomach without releasing substantial amounts of drug in the stomach (i.e., less than 10% release, 5% release and even 1% release in the stomach) and sufficiently disintegrating in the intestine tract (by contact with approximately neutral or alkaline intestine juices) to allow the transport (active or passive) of the active agent through the walls of the intestinal tract.

The enteric coating is typically although not necessarily a polymeric material. Preferred enteric coating materials comprise bioerodible, gradually hydrolyzable and/or gradually water-soluble polymers. The "coating weight," or relative amount of coating material per capsule, generally dictates the time interval between ingestion and drug release. Any coating should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the practice of the present invention. The selection of the specific enteric coating material will depend on the following properties: resistance to dissolution and disintegration in the stomach; impermeability to gastric fluids and drug/carrier/enzyme while in the stomach; ability to dissolve or disintegrate rapidly at the target intestine site; physical and chemical stability during storage; non-toxicity; ease of application as a coating (substrate friendly); and economical practicality.

Suitable enteric coating materials include, but are not limited to: cellulosic polymers such as cellulose acetate phthalate, cellulose acetate trimellitate, hydroxypropylmethyl cellulose phthalate, hydroxypropylmethyl cellulose succinate and carboxymethylcellulose sodium; acrylic acid polymers and copolymers, preferably formed from acrylic acid, methacrylic acid, methyl acrylate, ammonium methylacrylate, ethyl acrylate, methyl methacrylate and/or ethyl methacrylate (e.g., those copolymers sold under the tradename EUDRAGIT); vinyl polymers and copolymers such as polyvinyl acetate, polyvinylacetate phthalate, vinylacetate crotonic acid copolymer, and ethylene-vinyl acetate copolymers; and shellac (purified lac). Combinations of different coating materials may also be used. Well known enteric coating material for use herein are those acrylic acid polymers and copolymers available under the tradename EUDRAGIT from Rohm Pharma (Germany). The EUDRAGIT series E, L, S, RL, RS and NE copolymers are available as solubilized in organic solvent, as an aqueous dispersion, or as a dry powder. The EUDRAGIT series RL, NE, and RS copolymers are insoluble in the gastrointestinal tract but are permeable and are used primarily for extended release. The EUDRAGIT series E copolymers dissolve in the stomach. The EUDRAGIT series L, L-30D and S copolymers are insoluble in stomach and dissolve in the intestine, and are thus most preferred herein.

A particular methacrylic copolymer is EUDRAGIT L, particularly L-30D. In EUDRAGIT L-30D, the copolymer is known to be insoluble in gastrointestinal fluids having pH below 5.5, generally 1.5-5.5, i.e., the pH generally present in the fluid of the upper gastrointestinal tract, but readily soluble or partially soluble at pH above 5.5, i.e., the pH generally present in the fluid of lower gastrointestinal tract. Another particular methacrylic acid polymer is EUDRAGIT S, which differs from EUDRAGIT L-30D in that EUDRAGIT S is insoluble at pH below 5.5, but unlike EUDRAGIT L-30D, is poorly soluble in gastrointestinal fluids having a pH in the range of 5.5 to 7.0, such as in the small intestine. This copolymer is soluble at pH 7.0 and above, i.e., the pH generally found in the colon. EUDRAGIT S can be used alone as a coating to provide drug delivery in the large intestine. Alternatively, EUDRAGIT S, being poorly soluble in intestinal fluids below pH 7, can be used in combination with EUDRAGIT L-30D, soluble in intestinal fluids above pH 5.5, in order to provide a delayed release composition which can be formulated to deliver the active agent to various segments of the intestinal tract. The more EUDRAGIT L-30D used, the more proximal release and delivery begins, and the more EUDRAGIT S used, the more distal release and delivery begins. It will be appreciated by those skilled in the art that both EUDRAGIT L-30D and EUDRAGIT S can be replaced with other pharmaceutically acceptable polymers having similar pH solubility characteristics.

The enteric coating provides for controlled release of the active agent, such that drug release can be accomplished at some generally predictable location. The enteric coating also prevents exposure of the therapeutic agent and carrier to the epithelial and mucosal tissue of the buccal cavity, pharynx, esophagus, and stomach, and to the enzymes associated with these tissues. The enteric coating therefore helps to protect the active agent, carrier and a patient's internal tissue from any adverse event prior to drug release at the desired site of delivery.

The coating can, and usually does, contain a plasticizer to prevent the formation of pores and cracks that would permit the penetration of the gastric fluids. The coating can also contain other coating excipients such as detackifiers, antifoaming agents, lubricants, and stabilizers to solubilize or disperse the coating material, and to improve coating performance and the coated product. The coating can be applied to particles of the therapeutic agent(s), tablets of the therapeutic agent(s), capsules containing the therapeutic agent(s) and the like, using conventional coating methods and equipment. For example, an enteric coating can be applied to a capsule using a coating pan, an airless spray technique, fluidized bed coating equipment, or the like. Detailed information concerning materials, equipment and processes for preparing coated dosage forms may be found in Pharmaceutical Dosage Forms: Tablets, eds. Lieberman et al. (New York: Marcel Dekker, Inc., 1989), and in Ansel et al., Pharmaceutical Dosage Forms and Drug Delivery Systems, 6th Ed. (Media, Pa.: Williams & Wilkins, 1995). The coating thickness, as noted above, must be sufficient to ensure that the oral dosage form remains intact until the desired site of topical delivery in the lower intestinal tract is reached.

In another embodiment, drug dosage forms are provided that comprise a sustained release coated device housing a formulation of the invention. In this embodiment, the drug-containing formulation is encapsulated in a sustained release membrane or film. The membrane may be semipermeable, as described above. Semipermeable membrane allow for the passage of water inside the coated device to dissolve the drug. The dissolved drug solution diffuses out through the semipermeable membrane. The rate of drug release depends upon the thickness of the coated film and the release of drug can begin in any part of the GI tract. Suitable membrane materials for such a membrane include ethyl cellulose.

The therapeutic agents of the invention may be provided in capsules, coated or not. The capsule material may be either hard or soft, and as will be appreciated by those skilled in the art, typically comprises a tasteless, easily administered and water soluble compound such as gelatin, starch or a cellulosic material. The capsules are preferably sealed, such as with gelatin bands or the like. See, for example, Remington: The Science and Practice of Pharmacy, Nineteenth Edition (Easton, Pa.: Mack Publishing Co., 1995), which describes materials and methods for preparing encapsulated pharmaceuticals.

The compounds useful in the invention may be used alone, without other active agents. They also may be used together with other active agents, such as anti-inflammatory agents, anti-bacterial agents, or agents known useful in treating the conditions described herein such as agents useful for treating pouchitis. The agents may be delivered separately from one another or in the form of a cocktail of two or more agents. A cocktail is a mixture of any one of the compounds useful with this invention with another active agent.

Useful anti-inflammatory agents include, but are not limited to, non-steroidal anti-inflammatory drugs such as salicylic acid, acetylsalicylic acid, methyl salicylate, diflunisal, salsalate, olsalazine, sulfasalazine, acetaminophen, indomethacin, sulindac, etodolac, mefenamic acid, meclofenamate sodium, tolmetin, ketorolac, dichlofenac, ibuprofen, naproxen, naproxen sodium, fenoprofen, ketoprofen, flurbinprofen, oxaprozin, piroxicam, meloxicam, ampiroxicam, droxicam, pivoxicam, tenoxicam, nabumetome, phenylbutazone, oxyphenbutazone, antipyrine, aminopyrine, apazone and nimesulide; leukotriene antagonists including, but not limited to, zileuton, aurothioglucose, gold sodium thiomalate and auranofin; and other anti-inflammatory agents including, but not limited to, colchicine, allopurinol, probenecid, sulfinpyrazone and benzbromarone.

Other anti-inflammatory agents include Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Zomepirac Sodium.

Anti-bacterial agents include: Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylic acid; Aminosalicylate sodium; Amoxicillin; Amphomycin; Ampicillin; Ampicillin Sodium; Apalcillin Sodium; Apramycin; Aspartocin; Astromicin Sulfate; Avilamycin; Avoparcin; Azithromycin; Aziocillin; Aziocillin Sodium; Bacampicillin Hydrochloride; Bacitracin; Bacitracin Methylene Disalicylate; Bacitracin Zinc; Bambermycins; Benzoylpas Calcium; Berythromycin; Betamicin Sulfate; Biapenem; Biniramycin; Biphenamine Hydrochloride; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefmenoxime Hydrochloride; Cefinetazole; Cefinetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuroxime Pivoxetil; Cefuroxime Sodium; Cephacetrile Sodium; Cephalexin; Cephalexin Hydrochloride; Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphanilate; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofingin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isoconazole; Isepamicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Meziocillin; Meziocillin Sodium; Minocycline; Minocycline Hydrochloride; Mirincamycin Hydrochloride; Monensin; Monensin Sodium; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifuradene; Nifuraldezone; Nifuratel; Nifuratrone; Nifurdazil; Nifurimide; Nifurpirinol; Nifurquinazol; Nifurthiazole; Nitrocycline; Nitrofurantoin; Nitromide; Norfloxacin; Novobiocin Sodium; Ofloxacin; Ormetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine: Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate: Rosaramicin; Rosaramicin Butyrate; Rosaramicin Propionate; Rosaramicin Sodium Phosphate; Rosaramicin Stearate; Rosoxacin; Roxarsone; Roxithromycin; Sancycline; Sanfetrinem Sodium; Sarmoxicillin; Sarpicillin; Scopafingin; Sisomicin; Sisomicin Sulfate; Sparfloxacin; Spectinomycin Hydrochloride; Spiramycin; Stallimycin Hydrochloride; Steffimycin; Streptomycin Sulfate; Streptonicozid; Sulfabenz; Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter; Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline; Tetracycline Hydrochloride; Tetracycline Phosphate Complex;

Tetroxoprim; Thiamphenicol; Thiphencillin Potassium; Ticarcillin Cresyl Sodium; Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin: Vancomycin; Vancomycin Hydrochloride; Virginiamycin; Zorbamycin.

Figure 8:
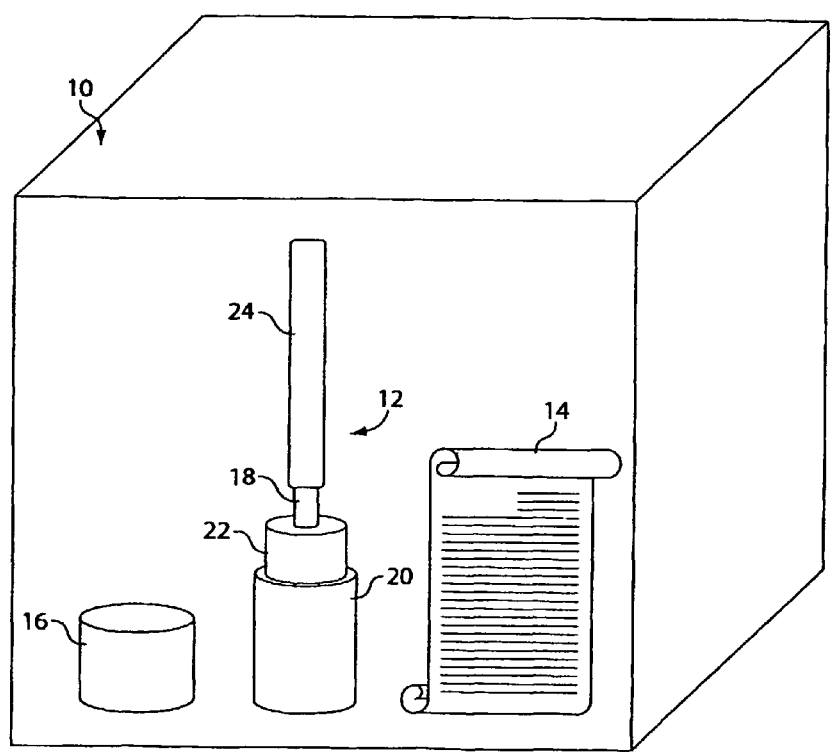
FIG. 8 is a schematic drawing of a kit according to the invention.

According to another aspect of the invention, a kit is provided (FIG. 8). A nonlatex, soft squeeze container having a conventional flow control and reflux prevention valve with an insertable enema tip covered by a removable protective shield is depicted. The kit 10 is a package containing an enema component 12, a package insert 14, and optionally a vial 16 containing one or more of the following: solvent, sterile solvent, antifungal azole compound or a second active agent. The enema component 12 includes in the depicted embodiment an insertable enema tip 18, a container 20 adapted for fluid connection to an insertable enema tip, a flow control and reflux-prevention valve 22 and a replaceable protective shield 24 for the enema tip 18. The container 20 contains an anti-fungal azole compound. The vial 16 contains a diluent for diluting the anti-fungal azole compound. The package insert 14 includes instructions for using the kit components according to the methods of the invention. The kit can optionally include a second vial (not shown) for a second active agent.

EXAMPLES

Example 1

Clotrimazole (CLT) Inhibits Human PMN Transmigration Across Cultured Intestinal Epithelia Recruitment of polymorphonuclear neutrophils (PMN's) across intestinal epithelia and into the lumen, resulting in mucosal ulcerations or frank crypt abscesses, occurs in a broad spectrum of infectious, inflammatory, and allergic diarrheal states, including patients with inflammation of surgically constructed ileal reservoirs ("pouchitis"). The transmigration of PMN's across the epithelial barrier represents the pathognomonic feature of acute and active chronic intestinal inflammation. Since CLT has been previously shown to inhibit PMN chemotaxis in-vitro, this study tested if CLT may also be efficacious in attenuating PMN transmigration in an established in-vitro model of colitis using intestinal T84 cell monolayers. As shown in FIG. 1, pretreatment of PMN's alone with CLT (30 μM) for 30 minutes inhibited significantly subsequent PMN transmigration. Of even greater interest, it was found that incubation of T84 monolayers alone with CLT, prior to layering of untreated PMN's, resulted in an inhibition of transepithelial migration to an equal or greater extent. These data report that CLT displays discrete and independent anti-inflammatory effects on human PMN's and intestinal epithelial cells.

Figure 2A:
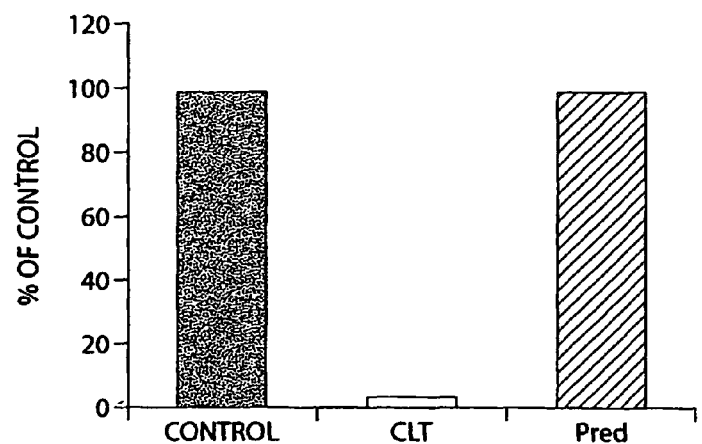
FIG. 2A is a bar graph that shows clotrimazole (CLT) and prednisone (Pred) inhibition of PMN transmigration.
Figure 2B:
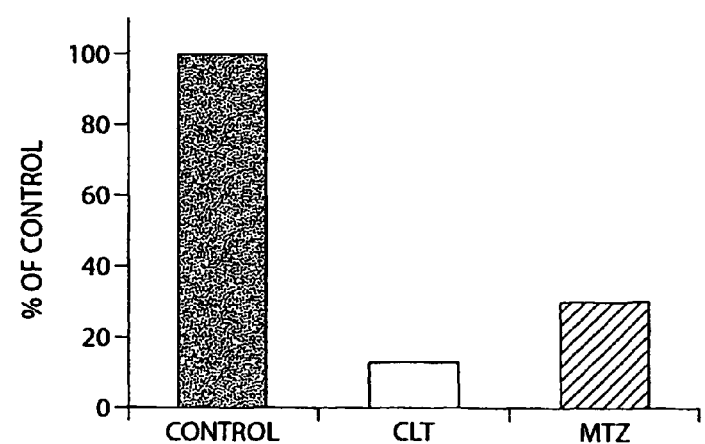
FIG. 2B is a bar graph that shows clotrimazole (CLT) and metronidazole (MNZ) inhibition of PMN transmigration.

The efficacy of CLT was compared to other antibiotic (metronidazole) and steroid (prednisone) agents that currently represent the standards of care for the topical or systemic therapy of pouchitis. In these studies, both PMN's and intestinal T84 cells were incubated with 30 μM of study drug for 30 minutes prior to initiating PMN transmigration. As reported in FIG. 2A, pretreatment of PMN's and intestinal epithelia with prednisone resulted in no attenuation of subsequent PMN transepithelial migration. Treatment with metronidazole resulted in approximately 30-40% inhibition, which is considerably less than that displayed consistently by CLT in this assay (FIG. 2B). These data suggest that the mechanism by which CLT inhibits PMN transmigration-mediated mucosal damage is likely to be fundamentally different from the way in which steroids exert anti-inflammatory effects. Moreover, these data suggest that CLT is more potent in reducing tissue PMN transmigration than another imidazole-containing agent currently in widespread use in the treatment of distal colitis and pouchitis disease. As such, topical CLT treatment represents an attractive alternative for patients whose pouchitis disease has proven to be refractory to standard antibiotic or anti-inflammatory regimens. CLT may inhibit PMN transmigration by inhibiting the operation of plasma membrane $K^+$ or $Ca^{++}$ channels that are likely required to accommodate the volume changes necessary for PMN transmigration through epithelial intercellular tight junctions.

Example 2

Figure 3:
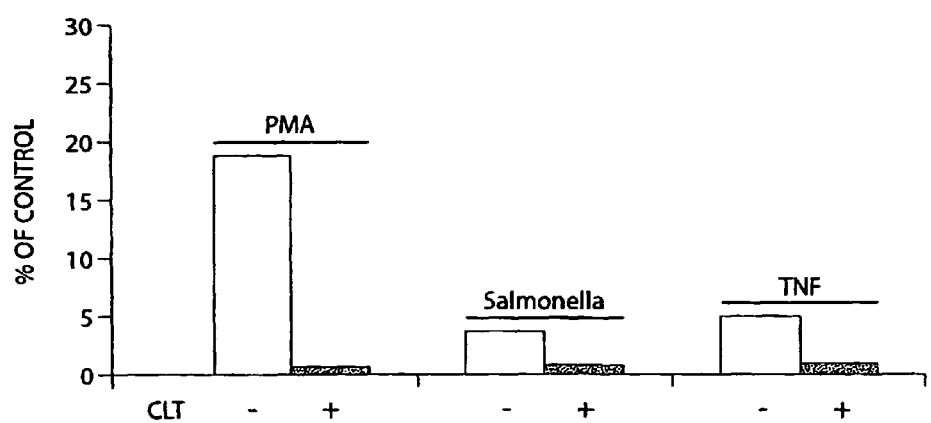
FIG. 3 is a bar graph that shows the effects of clotrimazole (CLT) on IL-8 secretion from cultured intestinal (T84) epithelia.

CLT Inhibits the Secretion of Pro-Inflammatory Cytokines by Intestinal Epithelia Intestinal epithelial cells play an active role in the mediation of intestinal inflammation through the production and regulated secretion of a variety of pro-inflammatory cytokines including IL-8. We tested whether CLT might also inhibit intestinal inflammation by blocking the secretion of the pro-inflammatory cytokine IL-8 from epithelial cells. In these experiments, cultured intestinal epithelial T84 cells were incubated for 30 minutes with CLT (30 μM) prior to stimulation with either the protein kinase C stimulator PMA, the pro-inflammatory cytokine TNF, or a strain of pathogenic *Salmonella typhimurium*. As demonstrated in FIG. 3, CLT pre-treatment inhibited completely IL-8 secretion elicited by each of the agonists tested. These data show that CLT is able to inhibit the expression or release of IL-8 stimulated by both $Ca^{++}$-dependent and independent pathways. Moreover, these data suggest that CLT inhibits intestinal epithelial IL-8 secretion by acting at distal steps in the signaling pathway, and likely at or near the level of NF-KB.

Example 3

CLT—Pharmacokinetics and Toxicity

Oral CLT Pharmacokinetics.

CLT is absorbed from the gastrointestinal tract after oral dosing. Intestinal absorption is enhanced by a high lipid intake, and blood levels 3-4 times higher than those obtained with tablet forms can be achieved if the drug is delivered in an oil solvent. There are marked inter-individual differences in the rate of CLT absorption, and plasma levels ranging from 1.6 to 4.0 μg/ml (4.6 to 11.6 μM) were measured 4-14 hours after oral administration of 1000 mg of CLT (corresponding to approximately 15 mg CLT/Kg body weight). Serum levels of 0.2-0.35 μg/ml were measured in adults after an oral dose of 200 mg of CLT. Most of these studies have estimated CLT blood levels based on biological methods rather than direct measurement. The HPLC assay utilized in this experiment detected and quantified plasma CLT levels that are below the sensitivity threshold for these previous biological assays.

Metabolism of CLT takes place principally in the liver, and only a small fraction of the drug is excreted unchanged in the urine. Most of the CLT metabolites excreted in the urine are biologically inactive, as judged by antifungal assays. CLT appears to be eliminated largely in the feces via biliary excretion. There is no existing data to suggest that CLT undergoes significant entero-hepatic circulation.

Oral CLT, Toxicity.

The LD$_{50}$ for oral CLT is in the range of 700-1,000 mg/Kg in mice, rats, and rabbits. Subacute and chronic toxicity in experimental animals involves the liver (degenerative changes) and the adrenal gland (increased fat deposition). These changes are reversible within 6 months of discontinuation of therapy.

Patients treated with oral CLT (60-90 mg/Kg body weight/day) were examined in a multicenter European trial for the treatment of deep-seated mycosis. 64% of patients enrolled in this study tolerated CLT therapy well. Another 18.5% tolerated CLT therapy moderately well, and only 6.5% found the therapy intolerable. 13% of patients reported gastrointestinal complaints (nausea, vomiting, and diarrhea), 4.4% developed chemical cystitis and 2.2% contact dermatitis.

A study in normal volunteers treated with oral CLT in oil form reported severe vertigo after a first dose of 1,000 mg. Vertigo worsened with accompanying hallucinations and anxiety after the second dose. All neurological symptoms disappeared within 24 hours after discontinuing CLT therapy. After one week of continued daily therapy with oral tablets, serum CLT levels seemed to decline in all treated patients. It is unclear as to whether or not this decline in serum concentrations while on therapy was due to the induction of hepatic microsomal enzymes by CLT or by the nausea induced by CLT, leading to a reduced intake of the drug by study subjects.

Topical CLT, Toxicity.

CLT has also been used in mucosal preparations (1% vaginal cream, 100 mg and 500 mg tablets) with clinical efficacy and minimal side effects. No central nervous system abnormalities have been reported following topical application of CLT. The most commonly reported adverse effects are local burning, and itching. Less common side effects include contact dermatitis, irritation, vulvar edema, dysuria, and dyspareunia. Subjects in our study evaluating the efficacy and safety of CLT suppositories reported none of these adverse effects. Absorption of CLT after vaginal application was estimated to be between 3 and 10%. While fungicidal concentrations of CLT were detected in vaginal fluid up to 3 days after application of one vaginal tablet, concurrent plasma levels were lower than 0.01 µg/ml.

Rectal CLT Delivered as a Suppository, Pharmacokinetics.

The safety and efficacy of topical CLT therapy was also evaluated (delivered as a rectal suppository) in pediatric and adult patients with active pouchitis. In this study, subjects progressed through three escalating dosing levels: Step A (500 mg rectal suppositories applied twice daily); Step B (750 mg rectal suppositories applied twice daily); Step C (1,500 mg delivered twice daily). Serum levels (measured using a previously validated HPLC assay) were obtained within 3 to 6 hours after administering the morning (8 AM) dose of CLT and are presented in Table 2.

TABLE 2

Serum CLT levels (µM) in adult and pediatric subjects with pouchitis treated with CLT suppositories

| Subject | Step A | Step B | Step C |
|---------|--------|--------|--------|
| BA | 0 | N/A | WD |
| JG | 0.8 | N/A | WD |
| JH | 0 | 0 | 0 |
| JI | 0 | N/A | WD |
| ER | 0 | 0 | 0 |

TABLE 2-continued

Serum CLT levels (µM) in adult and pediatric subjects with pouchitis treated with CLT suppositories

| Subject | Step A | Step B | Step C |
|---------|--------|--------|--------|
| ET | 0 | ND | WD |
| ZP | 0.38 | 0.8 | WD |
| DR | LE | LE | 0.34 |

ND = Not Done; WD = Withdrawn; N/A = subject withdrew from study prior to collection of Serum CLT level LE = Lab Error in Specimen Processing While there were some inter-individual differences, this data reported that there is generally poor systemic absorption (measured as serum CLT concentration) from ileal pouches. Moreover, the serum CLT levels observed were significantly lower than those reported in previous trials evaluating the efficacy of orally administered CLT. In previous studies evaluating the anti-inflammatory efficacy of oral CLT in the treatment of rheumatoid arthritis, adverse effects (nausea and reversible elevations in liver function tests) experienced by study subjects were dose limiting. As such, this data suggest that the therapeutic index for exploiting the anti-inflammatory properties of CLT is considerably broader when the drug is delivered topically into the rectum, in comparison to previous studies that have relied on its absorption and systemic tissue distribution.

Rectal CLT delivered as a suppository, toxicity. The clinical outcome for subjects enrolled in a study evaluating the safety and efficacy of CLT suppositories is included below in Table 3

TABLE 3

Clinical outcome of subjects treated with CLT suppositories

| Subject | Study Outcome (C) or (W) | Outcome/Reason |
|---------|--------------------------|----------------|
| DR | C | Pursued Off-Label Therapy |
| JH | C | Pursued Off-Label Therapy |
| ER | C | Improved Clinically |
| JG | W (Step B) | Gastric Dysmotility/Inc. Disease |
| ZP | W (Step B) | Renal Disease Detected |
| JI | W (Step B) | Worsening Ileitis |
| ET | W (Step B) | Increased Joint Pain |
| BA | W (Step B) | Inc Disease/Increased Anxiety |

C = Completed the Study; W = Withdrew from Study (During which Step)

(DR) Experienced a significant improvement in clinical symptoms and pursued off-label therapy for her refractory pouchitis with CLT suppositories.

(JH) Experienced a significant improvement in clinical symptoms and pursued off-label therapy for her refractory pouchitis with CLT suppositories.

(ER) Reported no significant adverse effect of CLT therapy, and she reported an overall clinical improvement by conclusion of the study.

(JG) Discontinued therapy when she perceived little clinical benefit and a sensation of poor gastric motility.

(ZP) Discontinued therapy when he was found to have renal disease (IgA nephropathy). There has been no previous report of CLT therapy causing IgA nephropathy or any other significant renal disease in humans, and it was not the impression of his renal physicians that his CLT study therapy had precipitated this complication. In contrast, oral CLT therapy has been used extensively in the past to treat fungal infections of the kidney with good results. IgA nephropathy is a well-reported complication occurring in patients with inflammatory bowel disease. The serum CLT level measured at the time of his renal diagnosis (0.08 µM) is far below that reported in previous studies using oral CLT therapy. No other subjects participating in the study demonstrated any significant changes in urinary sediment or serum BUN or creatinine values.

(JI) Discontinued therapy due to worsening mucosal inflammation. She had mucosal disease that extended beyond her ileal pouch at the time of study enrollment.

(ET) Discontinued therapy to begin systemic steroid therapy for worsening extra-intestinal symptoms (arthritis of his hips).

(BA) Discontinued therapy when he perceived a worsening of his colitis and a heightened sense of agitation/anxiety and chest pain. His serum CLT level was below the level of detection at the conclusion of Step A. He had discontinued therapy unannounced during Step B, and he presented for his interval visit long after (more that one week) measurement of a serum CLT level would have been relevant. As such, it is difficult to interpret his changes in affect without the benefit of either/both concomitant relevant laboratory values or a placebo arm for comparison.

These data demonstrate that topical CLT therapy (delivered as a rectal suppository) was generally well tolerated in the pediatric and adult patients studied.

Example 4

CLT Inhibits Intestinal Inflammation in Pouchitis, an In-Vivo Human Model of Intestinal Inflammation This study was an open-labeled, dose escalating trial evaluating the efficacy and safety of topical CLT suppositories in pediatric and adult patients with active pouchitis. In this study, subjects were treated with escalating doses of study drug: Step A (500 mg rectal suppositories applied twice daily); Step B (750 mg rectal suppositories applied twice daily); Step C (1,500 mg delivered twice daily). Few parameters were measured including fecal lactoferrin, a marker of white blood cell excretion, to assess the effects of topical CLT therapy on PMN transmigration in patients with pouchitis. This assay has been previously validated as a quantitative biochemical measure of PMN transmigration in patients with infectious colitis and inflammatory bowel disease. Data collected in this study are shown in Table 4 and show that topical CLT (delivered as a rectal suppository) is efficacious (reduced PMN excretion by 77% in 6 of 8 subjects that we studied) in treating PMN-mediated mucosal disease in patients with pouchitis.

TABLE 4

Response of fecal lactoferrin levels to treatment with CLT suppositories

| Subject | Baseline | Step A | Step B | Step C | Δ on Therapy |
|---|---|---|---|---|---|
| DR | 20.9 | 15.2 | ND | 2.2 | ↓ 89% |
| JH | 30.4 | 16.9 | 5.8 | 3.1 | ↓ 89% |
| ER | 45.1 | 30.3 | 66.2 | 26.2 | ↓ 41% |
| JG | 29 | 16.6 | 6.2 | 22.8 | ↓ 79%* |
| ZP | 20.8 | 15.2 | 180.3 | ND | ↑ 8X† |
| BA | 35.9 | 93.5 | ND | ND | ↑ 2.6X |

TABLE 4-continued

Response of fecal lactoferrin levels to treatment with CLT suppositories

| Subject | Baseline | Step A | Step B | Step C | Δ on Therapy |
|---|---|---|---|---|---|
| JR | 886.8 | 1227.3 | 199.3 | ND | ↓ 87% |
| ET | 1082.3 | 285.9 | ND | ND | ↓ 74% |

Δ = Change on Therapy;
ND = Not Done
*JG discontinued therapy after Step B. The final lactoferrin measurement (22.8) was recorded more than one week after her last dose of CLT. As such, the 79% reduction was calculated after completing Step B.
†This subject experienced an increase in FLA while on therapy, after demonstrating a 26% improvement during Step A. This high (180.3) value may be due to measurement error, subject variability, specimen handling, or true disease progression. His response was isolated, and data from other subjects is necessary to draw any meaningful conclusions.

Example 5

CLT Inhibits IL-8 Secretion in Calu-3 Cells but not in Calu-3 Cell Lysates

Calu-3 cells were plated at subconfluency onto Costar inserts (3.0 µm membrane pore size) using standard techniques. After 24 hours, the apical well media was aspirated, and the Calu-3 cells were permitted to grow at the air/media interface. Basolateral media was changed every 2-3 days until they had grown into confluent monolayers (typically 7-10 days). Pathogenic Salmonella typhi were grown in Luria's both overnight at 37° C. (on the night prior to experimentation). The bacteria were washed twice in approximately 20 ml Hanks Balanced Salt Solution (HBSS). Prior to use, bacteria were spun down and resuspended in a total of 10 ml HBSS.

On the day of experimentation, inserts were washed in HBSS and placed into wells containing HBSS with either vehicle (0.0015% ethanol) or 30 µM of specific imidazole or non-imidazole containing test compound (all compounds were diluted from 20 mM working stock). 200 µL of bacteria were then loaded onto the apical compartment, and the cells were allowed to incubate for 5 hours. The basolateral buffer solutions from each insert were subsequently aspirated into eppendorfs and stored at −20° C. Calu-3 filters were cut and rotated for 30 minutes in 250 µL of lysis buffer [10 mL of PBS containing 1 Complete Protease Inhibitor Cocktail Tablet (Roche Pharmaceuticals) tablet and 1 mN NaF] at 4° C., spun at 14,000 for 20 minutes, and the clarified supernatant was stored at −20° C. Supernatant and lysate IL-8 protein content was measured by ELISA using standard techniques.

Figure 4:
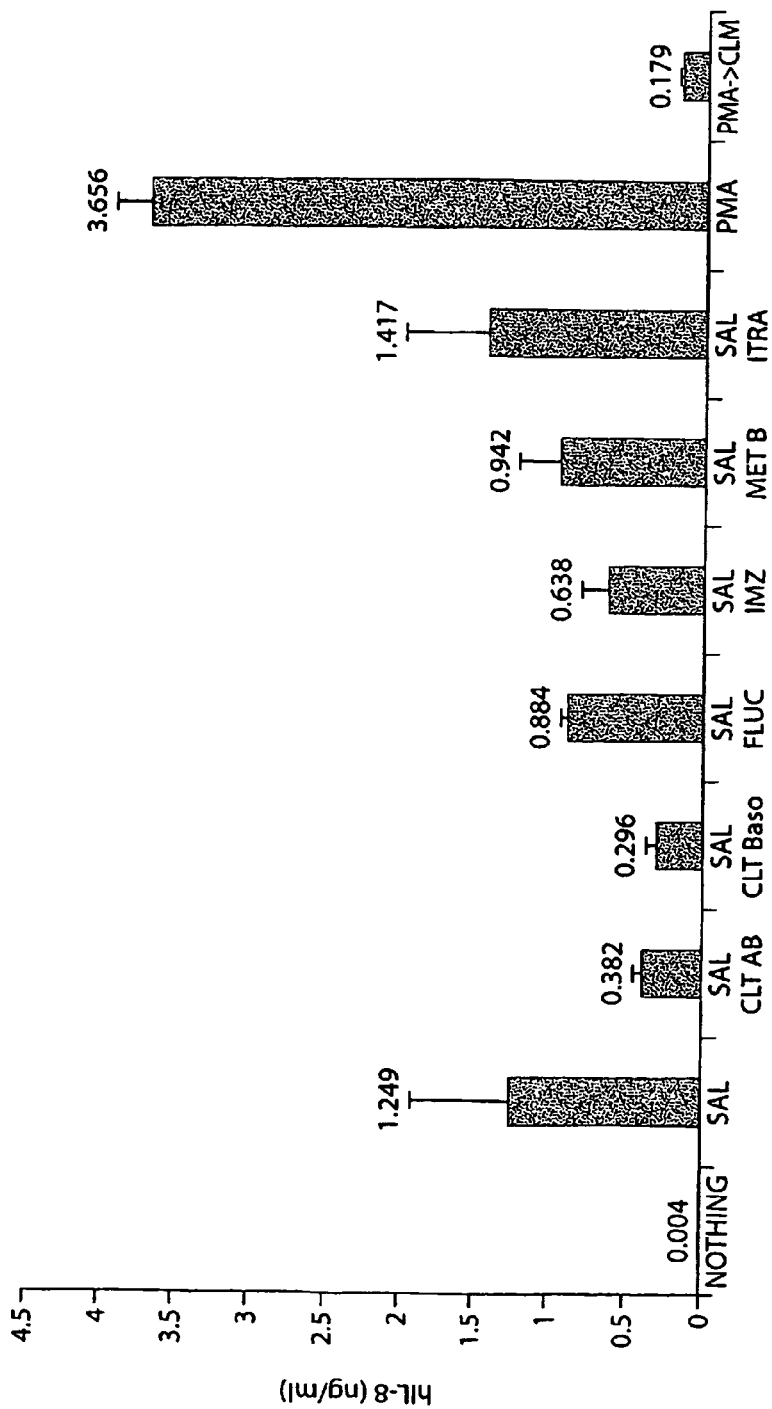
FIG. 4 is a bar graph that shows secreted IL-8 detected in basolateral supernatants of Calu-3 cells treated with saline (SAL), saline and clotrimazole (CLT), saline and fluconazole (FLUC) saline and imidazole (IMZ), saline and metabolite B (MET B), saline and itraconazole (ITRA), PMA, PMA followed by clotrimazole (CLT).

High level of IL-8 inhibition was observed when Calu-3 cells were stimulated with Salmonella and treated with CLT apically and basolaterally or just basolaterally alone (FIG. 4). Considerably less inhibition of IL-8 was observed when Calu-3 cells were treated with equimolar (30 µM) concentrations of fluconazole, imidazole, or metabolite b (the imidazole-free compound). No inhibition (or maybe even increased secretion) with was observed with itraconazole (FIG. 4).

Figure 5:
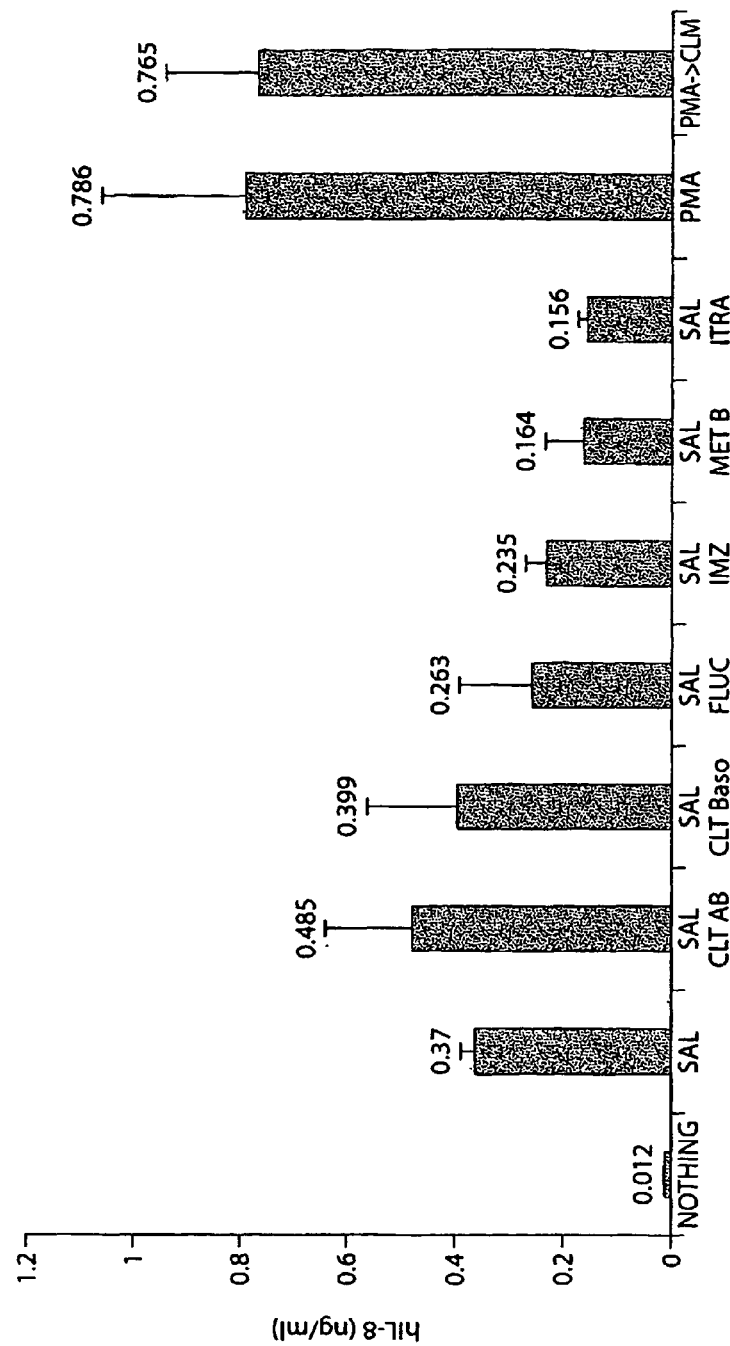
FIG. 5 is a bar graph that shows IL-8 within Calu-3 cells treated with saline (SAL), saline and clotrimazole (CLT), saline and fluconazole (FLUC) saline and imidazole (IMZ), saline and metabolite B (MET B), saline and itraconazole (ITRA), PMA, PMA followed by clotrimazole (CLT).

There was virtually no decrease in IL-8 in Calu-3 cells lysates in response to CLT treatment (FIG. 5). There was a slight inhibition with Metabolite B and itraconazole (but the IL-8 is being secreted out of the cells in these conditions). There was no effect of CLT on intracellular IL-8 in response to PMA stimulation. This was especially evident when compared relative to the discrepancy in IL-8 secreted in response to PMA.

Figure 6:
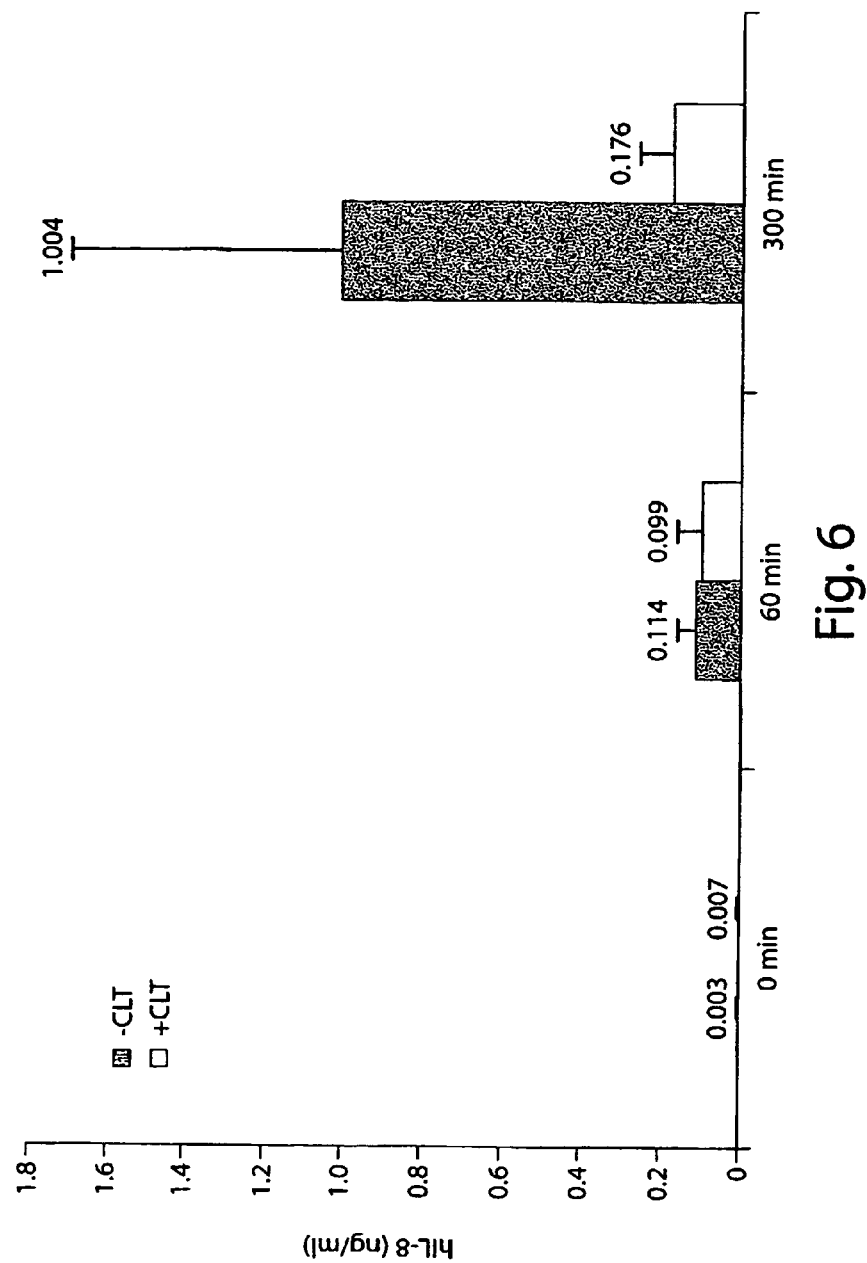
FIG. 6 is bar graph that shows the effect of clotrimazole on IL-8 in Calu cell supernatants.
Figure 7:
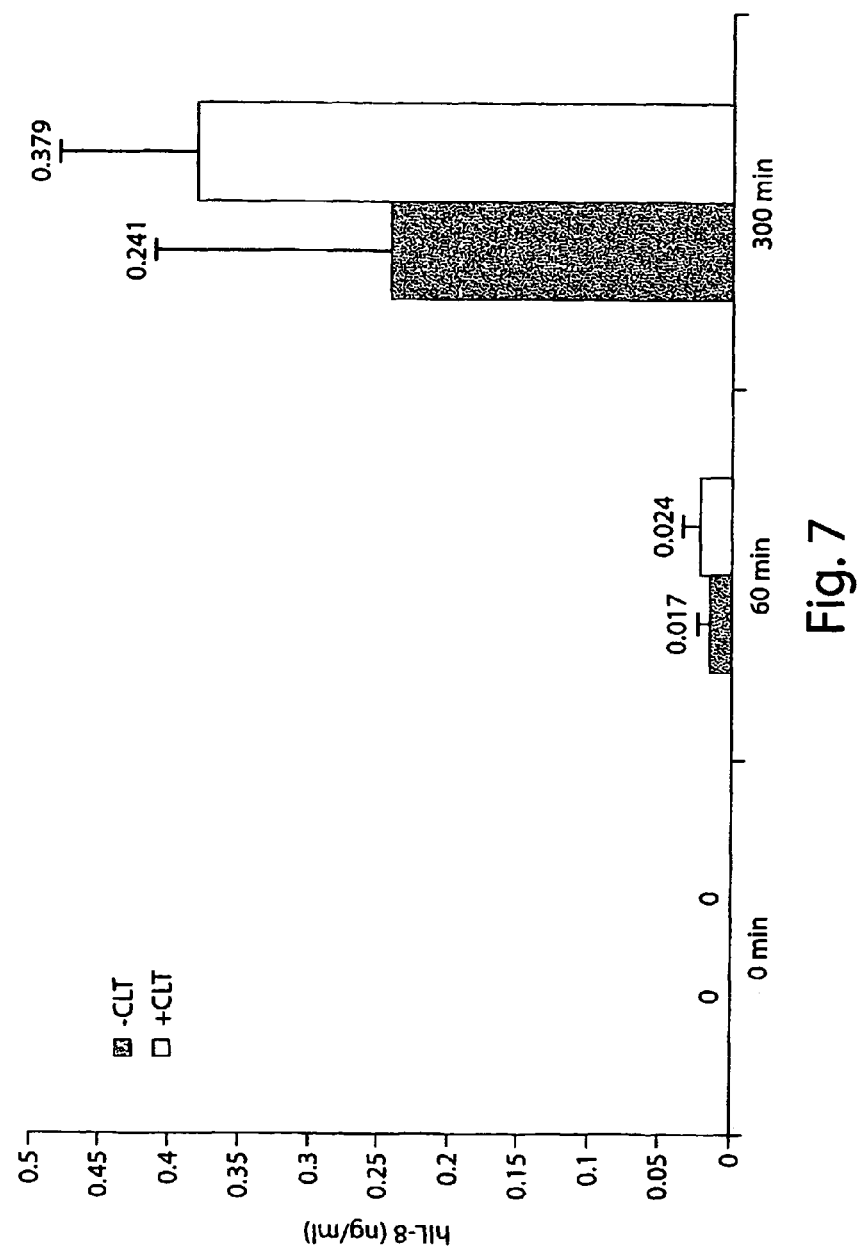
FIG. 7 is bar graph that shows the effect of clotrimazole on IL-8 in Calu cell lysates.

FIGS. 6 and 7 show the time-course of the data presented in FIGS. 4 and 5. There was very little IL-8 within the Calu-3 cells or in the supernatant at time 0. At 5 hours, there was a lot of IL-8 within the Calu-3 cells in treated and untreated cells. However, there was no IL-8 in the supernatants of Calu-3 cells pretreated with CLT. Metabolite B (an imidazole-free derivative of CLT) is less effective than CLT in inhibiting IL-8 secretion.

Example 6

CLT Enema Therapy for Treatment of Pouchitis

This study evaluated the efficacy and the safety of topical CLT therapy in enema preparations for the treatment in pediatric and adult patients with active pouchitis. The CLT retention enemas were prepared according to the following recipe:
1. Prepare 2% Methylcellulose Gel:
2. Measure 2 grams of Methocel E4M Premium USP Grade powder (PCCA Corp., Houston, Tex.).
3. Measure 98 ml of Purified Water USP and divide this volume in half. Put one half (48 ml) in the refrigerator and heat the other half (48 ml) with stirring until it just becomes steamy (65°-70° C.).
4. Slowly add the Methocel E4M to the heated Purified Water using a tea strainer to avoid clumping.
5. When the Methocel E4M is dispersed and free of clumps, take off the heat and add the refrigerated Purified Water and stir for 15 seconds. Place in refrigerator for 45 minutes and allow complete gelling.
6. Methocel Gel can be preserved by the addition of 0.2% Sodium Benzoate (PCCA Corp., Houston, Tex.).
7. Measure out the appropriate amount of CLT powder (2500, 4000, 6000, 7500 mg for adults; dosed proportionate to weight in pediatric patients, PCCA Corp., Houston, Tex.). Titrate the powder as needed to reduce particle size.
8. Wet CLT powder with enough Glycerin (PCCA Corp., Houston, Tex.) to make a smooth paste.
9. Slowly add Methylcellulose Gel (2%) to paste and bring to a total volume of 50 ml.
10. Shake well.
11. Transfer to plastic enema bottles.
12. Complete all labeling and manufacturing records.

The CLT enemas were administered once a day at night, and the patients received 2500-4000 mg of CLT in a retention enema with 60 ml of fluid. The gathered data is shown in Table 5:

TABLE 5

Gender, racial and age composition of the subject population

|  | FREQUENCY | PERCENT |
|---|---|---|
| GENDER |  |  |
| Male | 5 | 55.56 |
| Female | 4 | 44.44 |
| RACE |  |  |
| White, no other checked | 7 | 77.78 |
| Black, no other checked | 2 | 22.22 |

| AGE | n | MEAN | sd | MEDIAN | MIN | MAX |
|---|---|---|---|---|---|---|
| All | 9 | 39.0 | 20.0 | 46.0 | 10.2 | 64.4 |
| Non-adult | 2 | 12.7 | 3.5 | 12.7 | 10.2 | 15.2 |
| Adult | 7 | 46.5 | 15.4 | 49.0 | 24.8 | 64.4 |

The PDAI was determined for the patient population following the CLT topical retention enema treatments. PDAI is the Pouchitis Disease Activity Index. This is a validated composite score that included clinical (how does the patient feel), endoscopic (how does the pouch look), and histologic (what do we see under the microscope). The baseline data, as well as the net average change, drop by 3.8, is provided in Table 6:

TABLE 6

PDAI for patients treated with CLT retention enemas

| n | MEAN | sd | MEDIAN | MIN | MAX |
|---|---|---|---|---|---|
| PDAI BASELINE |  |  |  |  |  |
| 9 | 12.1 | 2.5 | 12 | 9 | 16 |
| PDAI CHANGE |  |  |  |  |  |
| 9 | −3.8 | 1.8 | −5 | −6 | −1 |

With respect to falling PDAI scores, 3 subjects had a 2 point or less drop in their score, and 6 patients had a drop in score of 3 or more, as shown in Table 7:

TABLE 7

PDAI DROP

| DROP | FREQUENCY | PERCENT |
|---|---|---|
| 2 pt or less | 3 | 33.33 |
| 3 pt or more | 6 | 66.67 |

In addition to efficacy data, safety data was also gathered for the use of CLT in retention enemas administered daily in a dose of 3500-4000 mg in the same group of patients. The following parameters were measured: urea nitrogen, Creatinine, aspartate aminotransferase (AST or SGOT), alanine aminotransferase (ALT or SGPT), alkaline phosphatase (Alk Phos), Total Bilirubin, Direct Bilirubin, Albumin, and Hematocrit. The results of the safety studies are summarized in Table 8:

TABLE 8

Safety data for CLT therapy in retention enemas

| PERIOD | n | MEAN | sd | MEDIAN | MIN | MAX |
|---|---|---|---|---|---|---|
| UREA NITROGEN (BUN), mg/dl |  |  |  |  |  |  |
| Baseline | 9 | 13.3 | 3.2 | 14.0 | 9.0 | 19.0 |
| Change | 9 | 0.1 | 2.6 | 0.0 | −5.0 | 4.0 |
| CREATININE, mg/dl |  |  |  |  |  |  |
| Baseline | 9 | 0.8 | 0.1 | 0.8 | 0.7 | 1.1 |
| Change | 9 | −0.0 | 0.1 | −0.1 | −0.2 | 0.1 |
| SGOT (AST), U/L |  |  |  |  |  |  |
| Baseline | 9 | 21.9 | 8.5 | 23.0 | 11.0 | 36.0 |
| Change | 9 | −2.2 | 7.6 | −1.0 | −16.0 | 8.0 |
| SGPT (ALT), U/L |  |  |  |  |  |  |
| Baseline | 9 | 16.1 | 5.1 | 17.0 | 7.0 | 24.0 |
| Change | 9 | 0.9 | 4.0 | 0.0 | −6.0 | 8.0 |
| ALKALINE PHOSPHATASE, U/L |  |  |  |  |  |  |
| Baseline | 9 | 92.2 | 64.9 | 81.0 | 49.0 | 261.0 |
| Change | 9 | −2.4 | 25.0 | 1.0 | −60.0 | 37.0 |
| TOTAL BILIRUBIN, mg/dl |  |  |  |  |  |  |
| Baseline | 9 | 0.4 | 0.2 | 0.3 | 0.1 | 0.7 |
| Change | 9 | −0.0 | 0.2 | 0.0 | −0.5 | 0.2 |
| DIRECT BILIRUBIN, mg/dl |  |  |  |  |  |  |
| Baseline | 9 | 0.1 | 0.0 | 0.1 | 0.0 | 0.1 |
| Change | 9 | −0.0 | 0.1 | 0.0 | −0.1 | 0.1 |

TABLE 8-continued

Safety data for CLT therapy in retention enemas

| PERIOD | n | MEAN | sd | MEDIAN | MIN | MAX |
|---|---|---|---|---|---|---|
| ALBUMIN, G/DI | | | | | | |
| Baseline | 9 | 3.5 | 0.4 | 3.5 | 2.9 | 4.0 |
| Change | 9 | 0.1 | 0.4 | 0.0 | −0.4 | 1.1 |
| HEMATOCRIT, % | | | | | | |
| Baseline | 9 | 37.2 | 5.8 | 36.5 | 27.7 | 46.1 |
| Change | 9 | −0.5 | 3.3 | 0.5 | −4.7 | 5.9 |

Urinary parameters were also examined including urine glucose levels, urine protein levels, and urine hyaline casts and similarly to the other safety data no significant changes were reported (Table 9).

TABLE 9

Urinary parameters

| BASELINE FREQUENCY | FOLLOW-UP 0 | TOTAL |
|---|---|---|
| URINALYSIS GLUCOSE TABLE OF BASELINE BY FOLLOWUP | | |
| 0 | 9 | 9 |
| TOTAL | 9 | 9 |
| URINALYSIS PROTEIN TABLE OF BASELINE BY FOLLOW-UP | | |
| 0 | 8 | 8 |
| 1+ | 1 | 1 |
| TOTAL | 9 | 9 |
| URINE MICRO HYALINE CASTS TABLE OF BASELINE BY FOLLOW-UP | | |

| BASELINE | FOLLOW-UP | | | |
|---|---|---|---|---|
| FREQUENCY | 0-1 | None detected | Not done | TOTAL |
| 2-5 | 1 | 0 | 1 | 2 |
| Not done | 0 | 1 | 6 | 7 |
| TOTAL | 1 | 1 | 7 | 9 |

The next table gives a more precise report of subject responses during the study. 5 subjects experience a 5 or greater drop in their PDAI scores (Table 10). This is a level defined as clinically significant in this study.

TABLE 10

PDAI change

| ΔPDAI | FREQUENCY | % |
|---|---|---|
| −6 | 1 | 11.11 |
| −5 | 4 | 44.44 |
| −3 | 1 | 11.11 |
| −2 | 2 | 22.22 |
| −1 | 1 | 11.11 |

In summary, the study reported that CLT enema treatment for pouchitis was a safe and successful therapy.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method for treating a subject having non-fungal induced mucositis of the distal intestinal tract, comprising administering locally to the distal intestinal tract of the subject clotrimazole in an amount effective to reduce or eliminate the non-fungal induced mucositis of the distal intestinal tract, wherein the effective amount is administered in a single dosage in the range of 2,000 mg to 10,000 mg.

2. The method of claim 1, wherein the effective amount is administered at a frequency of administration from four times a day to once a month.

3. The method of claim 1, wherein the non-fungal induced mucositis of the distal intestinal tract is selected from the group consisting of pouchitis, ulcerative colitis, Crohn's disease, allergic colitis, autoimmune colitis, autoimmune enteropathy, bacterial colitis, diversion colitis and lymphocytic colitis.

4. The method of claim 1, wherein the non-fungal induced mucositis of the distal intestinal tract is pouchitis.

5. The method of claim 1, wherein the mucositis of the distal intestinal tract is non-microbial induced.

6. The method of claim 1, wherein the effective amount is from 2,500 mg to 10,000 mg at a frequency of from twice a day to once every two weeks.

7. The method of claim 1, wherein the subject is a human.

8. The method of claim 1, further comprising administering to the subject an amount of one or more non-azole compounds effective to treat the non-fungal induced mucositis of the distal intestinal tract.

9. The method of claim 8, wherein the non-azole compounds are selected from a list consisting of anti-inflammatory or anti-bacterial compounds.

* * * * *